United States Patent [19]

Liess et al.

[11] Patent Number: 4,727,879

[45] Date of Patent: Mar. 1, 1988

[54] MEASUREMENT DEVICE FOR INTRACARDIAL ACQUISITION OF BLOOD OXYGEN SATURATION

[75] Inventors: Hans-Dieter Liess, Muensing; Roland Heinze, Munich, both of Fed. Rep. of Germany

[73] Assignee: Siemens Aktiengesellschaft, Berlin and Munich, Fed. Rep. of Germany

[21] Appl. No.: 915,675

[22] Filed: Oct. 6, 1986

[30] Foreign Application Priority Data

Oct. 17, 1985 [DE] Fed. Rep. of Germany ....... 3537017
May 16, 1986 [DE] Fed. Rep. of Germany ....... 3616524

[51] Int. Cl.$^4$ ............................................. A61B 5/00
[52] U.S. Cl. ..................................... 128/633; 128/666
[58] Field of Search ........................ 128/633, 666, 665

[56] References Cited
U.S. PATENT DOCUMENTS 3,815,583 6/1974 Scheidt ............................ 128/666
4,399,820 8/1983 Wirtzfeld et al. .

Primary Examiner—Kyle L. Howell
Assistant Examiner—John C. Hanley
Attorney, Agent, or Firm—Hill, Van Santen, Steadman & Simpson

[57] ABSTRACT

A measurement device for frequency control of a heart pacemaker based on the level of blood oxygen saturation contains a measuring probe which includes a light transmitter and a light receiver. The light receiver receives the light emitted by the light transmitter and reflected by the blood. The light transmitter and the light receiver are connected in parallel to an evaluation circuit via two common lines, this evaluation circuit charging the measuring probe with a constant current or with a constant voltage. A resistor is arranged in series with the light receiver. A transistor is arranged parallel to this series circuit, the base thereof being connected to the junction of the resistor and the light receiver. By means of this arrangement, the measurement sensitivity given deposits on the probe is maintained at a higher level. In an alternative embodiment, this can also be achieved using a resistor in series with the light transmitter with a transistor controlled by the light receiver connected in parallel therewith.

12 Claims, 6 Drawing Figures

MEASUREMENT DEVICE FOR INTRACARDIAL ACQUISITION OF BLOOD OXYGEN SATURATION

BACKGROUND OF THE INVENTION

1. Field of the Invention

The invention relates to a measurement device for intracardial acquisition of blood oxygen saturation for frequency control of a heart pacemaker having a measuring probe which contains a light transmitter and a light receiver.

2. Description of the Prior Art

A blood saturation measuring device is described in U.S. Pat. No. 4,399,820 wherein the light receiver receives the light emitted by the light transmitter and reflected by the blood, and wherein the light transmitter and the light receiver are connected to an evaluation circuit via two common lines, this evaluation circuit charging the measuring probe with a constant current or with a constant voltage.

Such a measuring device is schematically shown in FIG. 1. The measuring probe contains a combination composed of a light-emitting diode 6 and a phototransistor 7 which are connected parallel such that the forward current through the light-emitting diode 6 is additively superimposed with the current through the phototransistor caused by the light action. The resistor 8 represents the resistance of the lead. Given drive of the measuring probe by the evaluation circuit A with a constant current or with a constant voltage, the light reflected by the blood dependent on its oxygen saturation triggers a current flow in the phototransistor 7 which effects a change of current or voltage at the measuring probe. The voltage current change generated by the light reflection is identified in an evaluation circuit by comparing the measured signal given a driven light-emitting diode and phototransistor to a reference signal.

FIG. 2 shows a current-voltage characteristic of the measuring probe of FIG. 1. The curve without current through the photo transistor 7, i.e., without reflection, is referenced I. The curve I' then arises with reflection.

The specific sensitivity E of the probe as a function of the blood oxygen saturation $SO_2$ is an important criterion for the measurement. Given operation with constant current, this shall be referred to below as $E_i$ and shall be referred to as $E_u$ given operation with constant voltage. Thus defined (with units identified in brackets) are:

given constant probe current: $i_s = i_k$ $$E_i = \frac{du_s}{ds_{O2}} \quad \frac{[mV]}{\%} \quad (1)$$

given constant probe voltage: $U_S = U_K$ $$E_u = \frac{di_s}{ds_{O2}} \quad \frac{[mA]}{\%} \quad (2)$$

wherein, in accord with FIG. 2,:
$u_s$ [mV] = Voltage at the probe (Sensor + Lead)
$i_s$ [mA] = Current through the probe (Sensor + Lead)

$$S_{O2}[\%] = \frac{HbO_2}{Hb + HbO_2},$$

Proportion of oxygenated hemoglobin (Hb) in the overall hemoglobin ($Hb + HbO_2$), i.e.: blood oxygen saturation When the specific sensitivity is calculated in accord with FIG. 2, then $$E_i = -i_k \cdot \frac{1}{L_D} \cdot \frac{1}{(1+K)^2} \cdot \frac{dK}{ds_{O2}} \quad (3)$$

and $$E_u = u_{K'} \cdot L_D \cdot \frac{1}{[1 + R_D L_D \cdot (1+K)]^2} \cdot \frac{dK}{ds_{O2}} \quad (4)$$

whereby:
$R_D$ [$\Omega$] = Series resistance of the light-emitting diode 6.

$$L_d[\Omega] = \frac{1}{R_{LED} + R_D} =$$

Slope of the current-voltage characteristic of the light-emitting diode 6 or, respectively, of the sensor given $K = 0$.
$u_{K'}[V] = u_K - u_D$ = Constant voltage, whereby $u_D$ is the forward voltage of the light-emitting diode 6.
$R_L[\Omega]$ = Lead resistance to the sensor.
$K1/100 = \cdot K[\%]$ = Optical coupling factor, dependent on the type of photo element, on the sensor geometry, deposits on the sensor and on the oxygen saturation.

$$\frac{dk}{dS_{O2}} =$$

Change of the coupling factor dependent on $S_{O2}$

It may be seen from equations (3) and (4) that the sensitivity of the probe in both operating conditions decreases with an increasing coupling factor K, a behavior characteristic only for this two-pole embodiment of the reflection probe. As long as k < 10%, i.e. K < 0.1, the measuring behavior of the probe is unproblematical. Fundamentally, however, an optimally high coupling factor is desired in order to save current and in order to achieve a high $SO_2$ sensitivity since, of course, $K \sim S_{0.2}$, so that the probe advantageously operates in the limit region $K \sim 0.1$. The problem thus arises that changes in the reflection space which increase K lead to a noticeable reduction of the probe sensitivity. Such a modification occurs given blood or tissue deposits on the probe which unavoidably occur given intracardial implantation. The deposits reduce the sensitivity of the probe not only by damping the transition of the light between the sensor and blood and, thus, the factor $(dk/dS_{O2})$ but also by changing K as a consequence of the light reflection at the deposit which is not $S_{O2}$- dependent, referred to below as "zero reflection".

The decrease in the sensitivity can also be explained because, in the known arrangement, the transmission current flowing through the light transmitter is reduced by the reception current flowing through the light receiver, thus that much less transmission current is available given increasing zero reflection.

FIG. 3 shows the standardized sensitivity $E_{ni}$ for constant current operation dependent on deposits having the thickness d at the measuring probe. The sensitivity $E_{ni}$ is thereby standardized such that the value I is without deposits. The curve III is valid for the prior art. The great decrease of the sensitivity with increasing deposits is thereby clearly visible. This decrease of the sensitivity creates problems with respect to the resolution range of the measuring amplifier. In order to keep the circuit outlay from becoming excessively high, measuring amplifiers having too high a dynamic range cannot be employed.

SUMMARY OF THE INVENTION

It is therefore the object of the invention to provide a measurement device of the type described above wherein the decrease in sensitivity caused by deposits on the measuring probe is reduced.

This object is achieved in a first embodiment wherein a transistor circuit is arranged parallel to the light transmitter, this transistor circuit being controlled such by the light receiver such that its current consumption decreases with increasing light incidence.

Zero reflections thus effect a decrease in the slope of the current/voltage characteristic of the measuring probe, i.e., an increasing sensitivity. Given deposits, thus, the sensitivity now only decreases on the basis of attenuations of the light transmission path, whereby a smaller reduction of the sensitivity derives due to deposits than given the prior art.

In a further embodiment a first resistor is arranged in series with the light transmitter, an element controllable dependent on the light reflected by the blood being connected parallel to this first resistor. The reception current is thereby prevented from being reduced with increasing reflection of the transmission current, so that a smaller diminution of the sensitivity occurs given deposits.

The idea of avoiding a reduction of the transmission current by the reception current in order to resolve the object is shared by both embodiments.

In another embodiment, a second resistor is arranged in series with a light receiver and a transistor, whose control terminal is connected to the junction of the second resistor and of the light receiver, is arranged parallel to this series connection. This means that this junction, with a bipolar transistor, is connected to the base thereof, and with a field effect transistor is connected to the gate thereof.

A first resistor is preferably arranged in series with the light transmitter. The current/voltage curve in the constant current mode thus becomes more flat overall and the arrangement becomes more sensitive.

A simple circuit in accord with the second embodiment includes a second resistor is arranged in series with the light receiver, and the controllable element is a transistor whose base is connected to the junction of the light receiver and the second resistor.

DESCRIPTION OF THE PREFERRED EMBODIMENTS

Figure 1:
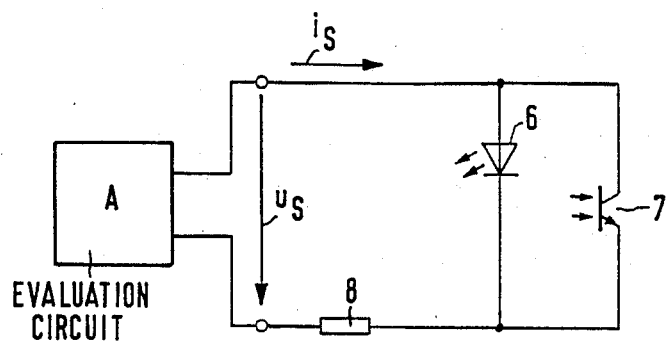
FIG. 1 is a schematic circuit diagram of a measuring probe constructed in accordance with the teachings of the prior art.
Figure 2:
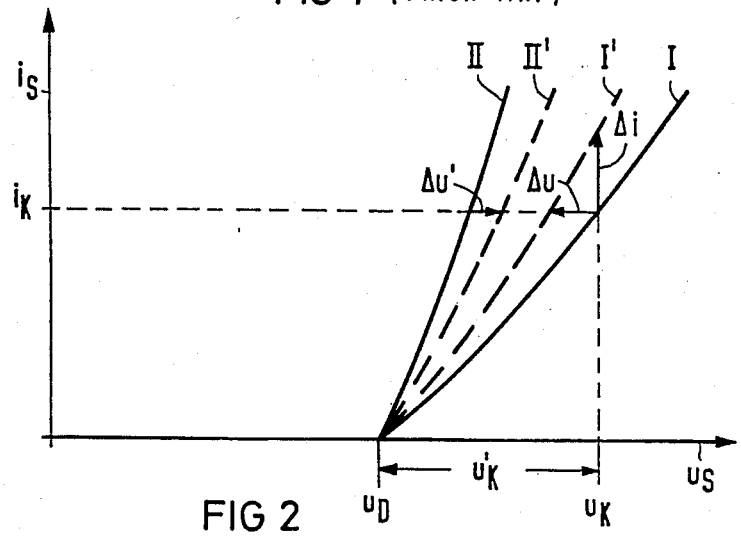
FIG. 2 shows a series of current/voltage curves comparing prior art measuring probes and a measuring probe constructed in accordance with the principles of the present invention.

An exemplary embodiment of the invention based on the first alternative solution shall be set forth in greater detail below with reference to FIG. 4. Since it has proven advantageous in practice to drive the measuring probe with constant current because the lead resistance $R_L$ referenced is thereby without influence on the sensitivity, the circuit comprising series resistor $R_D$ referenced shall be discussed below. The measuring probe S contains the parallel connection of a transistor 3, a series circuit of a resistor 4 and a light-sensitive diode 2 as light receiver, as well as of the resistor 5 and a light-emitting diode 1 as the light transmitter. The measuring probe S is charged with a constant current by an evaluation circuit A. The current flow through the light-sensitive diode 2 thereby becomes greater with increasing reflection of the light at the blood dependent on the oxygen saturation of the blood. The current supplied to the base of transistor 3 via the resistor 4 is thereby reduced, so that its conductivity decreases. When, for example, the measuring probe S without reflection has the current/voltage curve referenced II in FIG. 2, then it exhibits the curve referenced II' with reflection. Given drive with constant current $i_s = i_k$ the voltage increases by $\Delta U$. The current/voltage curve $\Delta I/\Delta U$ becomes more flat and thus the arrangement becomes more sensitive.

Figure 3:
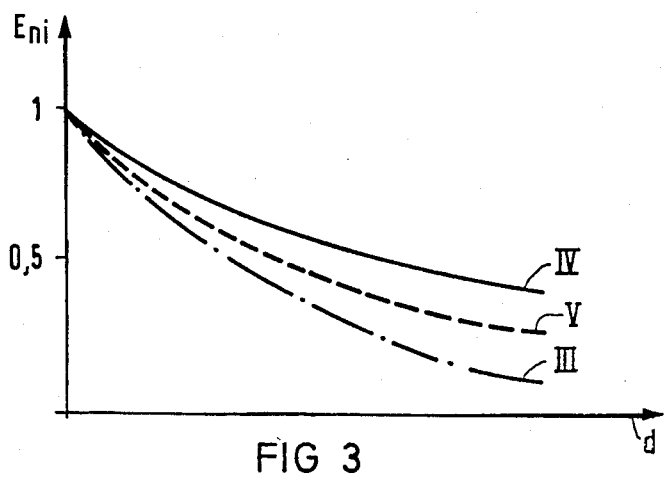
FIG. 3 shows curves of sensitivity versus probe disturbances for prior art measuring probes and two embodiments of the measuring probe constructed in accordance with the principles of the present invention.

In FIG. 3, the dependency of the standardized sensitivity $E_{ni}$ dependent on deposits d is referenced IV. The decrease of the sensitivity $E_{ni}$ given deposits is now caused only by attenuations on the transmission path and is significantly lower than in the prior art.

An increase in the sensitivity of the arrangement is also achieved with the resistor 5 since this likewise effects a flattening of the curve $\Delta I/\Delta U$.

Figure 5:
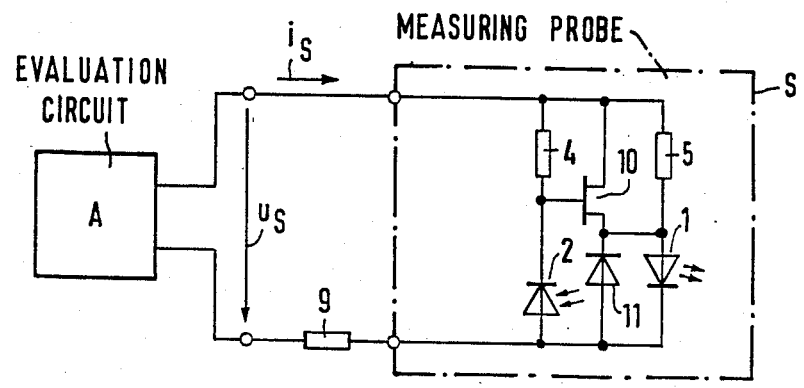
FIG. 5 is a schematic circuit diagram of a second embodiment of a measuring probe constructed in accordance with the principles of the present invention.

FIG. 5 shows an exemplary second embodiment of the invention. The series connection of a resistor 4 and a photodiode 2 as well as a resistor 5 and a light-emitting diode 1 are connected parallel in the measuring probe S. In addition, the resistor 5 has a field effect transistor 10 connected in parallel therewith, the gate of the latter being connected to the junction of the resistor 4 and the photodiode 2. The light-emitting diode 1 has a diode 11 connected in parallel therewith whose conductive direction is opposite that of the conductive direction of the light-emitting diode 1.

When, given this circuit, the light reflection at the blood increases, the power consumption of the photodiode 2 increases. The resistance of the field effect transistor 10 is thereby reduced, so that the current flowing through the light-emitting diode 1 is not reduced overall by the reception current flowing through the photodiode 2 as in conventional devices. It thus follows—as in the first embodiment—that a more neutral behavior of the sensitivity than in the prior art occurs given deposits at the probe and thus an increasing zero reflection. The change of the standardized sensitivity $E_n$, dependent on deposits d, is indicated with broken lines in FIG. 3 and is referenced V. One can see that the decrease of the sensitivity is noticeably less than given the known arrangement identified with III but is somewhat greater than in the first embodiment referenced IV.

Figure 4:
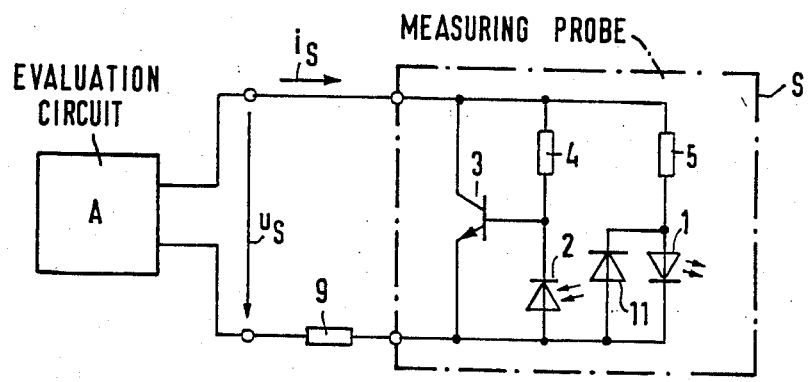
FIG. 4 is a schematic circuit diagram of a first embodiment of a measuring probe constructed in accordance with the principles of the present invention.

The diode II in the circuits of FIGS. 4 and 5 serves the purpose of reference measurement. For reference measurement, the current direction is reversed so that current no longer flows through the transmission diode 1. One thus obtains a measured variable which is independent of the reflected light and only depends on the lead resistance 9 and on the temperature of the measuring probe. This reference measurement can be employed for compensation of these influences on the measurement.

Figure 6:
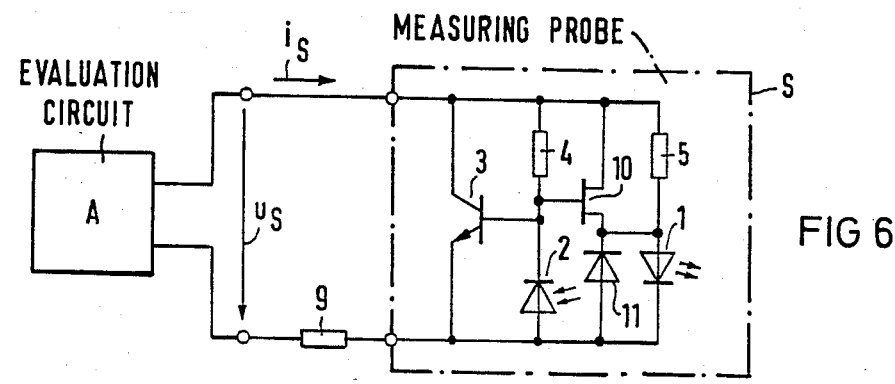
FIG. 6 is a schematic circuit diagram of a third embodiment of a measuring probe constructed in accordance with the principles of the present invention.

The exemplary embodiment of FIG. 6 represents a combination of the exemplary embodiments of FIGS. 4 and 5. In comparison to the circuit of FIG. 5, a transistor 3 is connected in parallel with the measuring arrangement as in the exemplary embodiment of FIG. 4. The conductivity of the transistor 3 becomes lower when the current through the photodiode 2 becomes greater. In this embodiment, the sensitivity decreases even less given deposits on the measuring probe.

Although modifications and changes may be suggested by those skilled in the art it is the intention of the inventor to embody within the patent warranted hereon all changes and modifications as reasonably and properly come within the scope of their contribution to the art.

We claim as our invention:

1. A probe for acquiring signals for intracardial measurement of blood oxygen saturation for use with an evaluation circuit having two outputs for charging said probe with a constant electrical operating parameter, said probe comprising:
    two input terminals connectable to evaluation circuit output terminals;
    a light transmitter means for transmitting light at blood connected across said input terminals;
    a light receiver means for receiving light from said light transmitter reflected by said blood connected across said input terminals; and
    a transistor means connected in parallel with said light transmitter for shunting current around said transmitter means and said receiver means; and
    means for decreasing the current conductability of said transistor means in response to any increase of current through said light receiver means.

2. A probe as claimed in claim 1, wherein said constant electrical operating parameter is current.

3. A probe as claimed in claim 1, wherein said constant electrical operating parameter is voltage.

4. A probe as claimed in claim 1, wherein said means for decreasing comprises:
    a resistor connected in series with said light receiver across said input terminals, and wherein the control terminal of said transistor is connected to the junction between said resistor and said light receiver means.

5. A probe as claimed in claim 1, further comprising a resistor connected in series with said light transmitter across said input terminals.

6. A probe as claimed in claim 5, wherein said light transmitter means is a device which conducts current in only one direction, and further comprising a diode connected in parallel with said light transmitter means in a direction for conducting current opposite to the current conducting direction of said light transmitter means.

7. A measuring probe for acquiring signals for intracardial measurement of blood oxygen saturation for use with an evaluation circuit having two outputs for charging said probe with a constant electrical operating parameter, said probe comprising:
    two input terminals connectable to evaluation circuit output terminals,
    a light transmitter means for transmitting light at blood connected across said input terminals;
    a light receiver means for receiving light from said light transmitter reflected by said blood connected across said input terminals;
    a resistor connected in series with said light transmitter means across said input terminals; and
    means connected across said resistor for conducting current in parallel to said resistor; and
    means for reducing the resistance of said means for conducting in response to any increase in current flow through said light receiver means.

8. A probe as claimed in claim 7, wherein said means for conducting comprises a transistor having a control terminal.

9. A probe as claimed in claim 8, wherein said means for reducing comprises a second resistor connected in series with said light receiver means across said input terminals, with said control terminal of said transistor being connected to the junction between said second resistor and said light receiver means.

10. A probe as claimed in claim 7, further comprising:
    a second resistor connected in series with said light receiver means across said input terminals; and
    a transistor connected in parallel with the series combination of said light receiver means and said second resistor and across said input terminals, said transistor having a control terminal connected to the junction between said second resistor and said light receiver means.

11. A probe as claimed in claim 7, wherein said light transmitter means is a device which conducts current in only one direction, and further comprising a diode connected in series with said means for conducting across said input terminals and further connected in parallel with said light transmitter means, said diode being connected for conducting current in a direction opposite to the current conducting direction of said light transmitter means.

12. A probe as claimed in claim 7, wherein said constant electrical operating parameter is voltage.

* * * * *